(12) United States Patent
Shimada et al.

(10) Patent No.: US 8,439,853 B2
(45) Date of Patent: May 14, 2013

(54) ELECTRIC MOXIBUSTION DEVICE

(75) Inventors: Osamu Shimada, Kumamoto (JP); Kenji Tsuda, Kumamoto (JP)

(73) Assignee: Kabushiki Kaisha S.F.C., Kumamoto (JP)

( * ) Notice: Subject to any disclaimer, the term of this patent is extended or adjusted under 35 U.S.C. 154(b) by 0 days.

(21) Appl. No.: 13/203,558

(22) PCT Filed: Feb. 12, 2010

(86) PCT No.: PCT/JP2010/000882
§ 371 (c)(1),
(2), (4) Date: Sep. 9, 2011

(87) PCT Pub. No.: WO2010/103730
PCT Pub. Date: Sep. 16, 2010

(65) Prior Publication Data
US 2011/0319818 A1  Dec. 29, 2011

(30) Foreign Application Priority Data

Mar. 9, 2009 (JP) ................................. 2009-054437

(51) Int. Cl.
*A61H 1/00* (2006.01)
*A61N 1/00* (2006.01)

(52) U.S. Cl.
USPC ............................................. 601/15; 607/3

(58) Field of Classification Search ................. 604/114; 607/96, 98–100, 3; 601/15
See application file for complete search history.

(56) References Cited

U.S. PATENT DOCUMENTS 5,931,806 A    8/1999  Shimada 6,251,380 B1*  6/2001  Jo ................................... 424/74
2009/0306607 A1  12/2009  Yasuhiro

FOREIGN PATENT DOCUMENTS

| JP | 58-105331 | 7/1983 |
| JP | 63-11035  | 1/1988 |
| JP | 3-53241   | 5/1991 |
| JP | 5-63546   | 8/1993 |
| JP | 5-95537   | 12/1993 |
| JP | 7-213582  | 8/1995 |
| JP | 10-230008 | 9/1998 |
| JP | 11-70175  | 3/1999 |

(Continued)

OTHER PUBLICATIONS

International Search Report issued Mar. 9, 2010 in International (PCT) Application No. PCT/JP2010/000882.

*Primary Examiner* — Laura A Bouchelle
*Assistant Examiner* — Melissa A Snyder
(74) *Attorney, Agent, or Firm* — Wenderoth, Lind & Ponack, L.L.P.

(57) ABSTRACT

An electric moxibustion device includes a tubular case having a front end opening, a heater unit placed near the front end opening in the case, and a heatproof rubber cap removably attached to the front end of the case. The heater unit comprises a heat transfer metal plate and a heating element which is fixed on the back surface of the heat transfer metal plate and generates heat using power from an external power source or a battery. The cap and the case are configured for holding an absorbent-retentive member which absorbs and retains a medical fluid between the discharge opening of the cap and the heat transfer metal plate in the case. The case has a thermoregulation circuit built-in which can change the temperature of the heating element in a stepwise manner, and push buttons for temperature adjustment are provided on the outer periphery of the case.

7 Claims, 3 Drawing Sheets

FOREIGN PATENT DOCUMENTS

| | | |
|---|---|---|
| JP | 2003-250860 | 9/2003 |
| JP | 3125048 | 8/2006 |
| JP | 3146429 | 10/2008 |
| WO | 2006/118226 | 11/2006 |

* cited by examiner

ELECTRIC MOXIBUSTION DEVICE

TECHNICAL FIELD

The present invention relates to an electric moxibustion device to apply electrically generated heat to an affected part instead of heat of burning moxa, particularly to a new electric moxibustion device which can permeate effective ingredients included in a medical fluid such as a loquat-leaf under the skin of the affected part, thereby providing excellent moxibustion treatment.

BACKGROUND ART

Conventionally, there have been many kinds of moxibustion devices which supply a thermal stimulus to an affected part to provide therapeutic effects such as promotion of blood circulation, removal of intramuscular wear, relief of the stiff muscles, ease of a neuralgia and muscular pain, activation of the gastrointestinal action.

Meanwhile, it is known that a raw loquat-leaf keeps the doctor away and is frequently used at various places. There are effective folk remedies, which are taught up to now and actually performed such as, for example, a method of repeatedly conducting the procedure to roast each front side of two loquat-leaves over a fire, then put the front sides together to rub against each other, and promptly put them on the affected part, another method which includes drinking a decocted loquat-leaf, and another method which includes a loquat-leaf warm bath. Relatively lately, it has been confirmed that a loquat-leaf includes the substance called "amygdalin" from which laetrile (vitamin B17) is extracted and that the laetrile is evaporated by heating to permeate in the body through the skin, thereby preferably purifying blood.

There is a moxibustion device, such as PLT 1, which provides treatment of burning moxa to supply the burning heat of the moxa on an affected part and simultaneously evaporating an extract of a raw loquat-leaf and the like by using the burning heat to permeate effective ingredients included in the moxa and loquat-leaf under the skin of the affected part.

The moxibustion device disclosed in PLT 1 has: a metal cylindrical body, having its surface covered with heat insulating material, in which moxa compressed and formed into a fairly hard bar-like shape can be slidably inserted; and a moxibustion cap member which is removably fit on the front end of the cylindrical body, provided with an outflow hole for the burning gas of moxa, and has a medical fluid evaporation chamber therein for filling up a member for absorbing and retaining a medical fluid such as a loquat-leaf extract.

With regard to the moxibustion device according to PLT 1, treatment is conducted by burning a bar-shaped moxa inserted in the cylindrical body, soaking a loquat-leaf extract or the like into the medical fluid absorbent-retentive member in the moxibustion cap before fitting the cap on the front end of the cylindrical body, and putting the gas outflow hole directly against the skin of an affected part. As using the burning heat of moxa for heating and evaporating the loquat-leaf extract soaked into the medical fluid absorbent-retentive member, the effective ingredients included in the moxa and loquat-leaf can sufficiently permeate under the skin of the affected part.

PTL1: JPY H02-38751

SUMMARY OF INVENTION

Technical Problem

In the conventional art, careful handling was required because of a fire generated by burning moxa. The conventional art also has problems such as, for example, the smoke generated by burning moxa might compel to abandon the use in some places, it was troublesome to dispose the moxa burned to ashes and to exchange medical fluid absorbent-retentive members, adjustment to the desired temperature was difficult, and if the burning of moxa was weak it was hard to evaporate the loquat-leaf extract.

In view of these facts, the present invention has the object to provide an electric moxibustion device which has high operability and safety and can efficiently and surely permeate effective ingredients of a loquat-leaf extract under the skin of an affected part.

Solution to Problem

An electric moxibustion device of the invention has a tubular case with an open front end, a heater unit placed near the front end opening in the case, and a heatproof rubber cap removably attached to the front end opening of the case, wherein:

the heater unit includes a heat transfer metal plate and a heating element which is fixed on the back surface of the heat transfer metal plate and generates heat by power feeding from an external power source or a battery;

the cap has a discharge opening for discharging heat from the heating element at the center of the front end thereof; and an absorbent-retentive member for absorbing and retaining a medical fluid such as a loquat-leaf extract is placed between the discharge opening of the cap and the heat transfer metal plate in the case. It should be understood that the case can be made of a square tube or polygonal tube as well as a cylindrical tube.

The electric moxibustion device makes it possible to raise the temperature of the heating element of the heater unit as a heat source only by switching ON/OFF the external power source or battery, and heat the absorbent-retentive member for the medical fluid such as a loquat-leaf extract through the heat transfer metal plate, thereby evaporating the absorbed, retained medical fluid such as a loquat-leaf extract.

Without burning moxa to avoid the use of fire, the moxibustion treatment is safe and used at any place because no smoke generates. For the use of an external power source, an outlet of commercial 100V power supply is enough, and when using a battery for power feeding, the device is available at the outdoors.

The device has also high operability at the time of use and maintenance because it is possible to supply a medical fluid such as a loquat-leaf extract even while in use, and exchange of medical fluid absorbent-retentive members only needs to remove the cap and place a new absorbent-retentive member between the heat transfer metal plate and the cap.

The electric moxibustion device of the invention is preferably provided with an ON/OFF switching button on the outer periphery of the case.

The electric moxibustion device like this is easy to turn on/off the power supply during the treatment. Even when switching off for supplying a medical fluid or exchanging absorbent-retentive members, for example, it is not necessary to pull out a power supply cord or remove a battery each time, so the operation is easy.

Further, the electric moxibustion device of the invention is preferably has a built-in thermoregulation circuit which can change the temperature of the heating element in a stepwise manner and also preferably has temperature adjustment push buttons provided on the outer periphery of the case.

The electric moxibustion device like this can make it possible for a user to select his/her favorite temperature to be used widely according to the applied part and to the individual heat sensitive difference, etc.

The electric moxibustion device of the invention is characterized in that powdered or granulated ore, which radiate a terahertz wave including far-infrared rays when heated, is burned into the surface of the heat transfer metal plate.

The terahertz wave here means an electromagnetic wave vibrating at the order of 1 trillion (T, $10^{12}$) per second and is considered to have properties to penetrate a substance like a radio wave and go straight on like a ray, because the frequency domain is 0.1-100 THz (terahertz). The terahertz domain is considered to include characteristic frequencies of all the living body on the earth and to be an electromagnetic wave which is safe and useful for the human body, therefore, a research to find a cancerous cell by using terahertz waves is carried on. The terahertz wave is understood not to destroy or damage a cell nucleus and a gene in a nucleus unlike a radiation, etc. but to have a function to adjust the distortion of a cell when penetrating to activate the cell. As is penetrative, the terahertz wave can warm the body thoroughly to the core, thereby activating the cell and blood, dilating the capillary, promoting the metabolism, raising immunity and spontaneous healing power, and discharging excessive fat and waste matter of the body together with sweat.

On the other hand, far-infrared rays is an electromagnetic wave included in the domain of a terahertz wave, but unlike the penetrative terahertz wave it is reflective and has a property to be partially absorbed into the vibration of a molecule composing the surface of a substance. When irradiated on the body, such far-infrared rays are absorbed near the surface of the body to warm the part.

As the electric moxibustion device of the invention has the heat transfer metal plate into the surface of which the powdered and granulated ore radiating terahertz waves including such far-infrared rays is burned, when heat is generated by electric conduction to the heating element during moxibustion treatment, the ore is heated through the heat transfer metal plate and radiates far-infrared rays and terahertz waves, which interact each other to warm both the surface part and core part of the body. In addition to it, the penetrative terahertz wave makes the extract of a loquat-leaf easy to permeate under the skin of the affected part, thereby further improving the moxibustion effects such as activation of cells and blood purification.

It is also preferable that a thin plate made of ore or powdered and granulated ore, which radiate terahertz waves including far-infrared rays when heated, is glued on the surface of the heat transfer metal plate.

In the electric moxibustion device of the invention, it is more preferable that the ore is Tenshoseki.

The Tenshoseki, 'Mitate Conglomerate' in scientific name, is an ore that has a highest clinical effect among above-mentioned ore radiating terahertz waves including far-infrared rays when heated, in view of activation of a cell and improvement of immunity. Therefore, the electric moxibustion device having the heat transfer metal plate into which such powdered and granulated Tenshoseki is burned, or the electric moxibustion device having the heat transfer metal plate on which the thin plate made of Tenshoseki itself or powdered and granulated Tenshoseki is glued can radiate far-infrared rays and terahertz waves when the heat transfer metal plate is heated by the heating element, thereby exhibiting the actions of far-infrared rays and of terahertz waves, together with the action of a loquat-leaf extract, to bring more preferable effects of moxibustion treatment.

The electric moxibustion device of the invention is further characterized in that negative ion together with terahertz waves including far-infrared rays is radiated from the surface of the heat transfer metal plate.

Tenshoseki is known to have an action to generate negative ion. When there is more ion in the body under the influence of exhaust gas, radiation, ultraviolet rays, etc., negative ion taken in the body improves the ion balance and acts to purify the blood, invigorate a cell, enhance the power of resistance, regulate the automatic nerve, and the like. That results in preferable effects such as the increase of appetite, reduction of blood pressure, relief of one's fatigue or the like. Therefore, in the moxibustion treatment by the electric moxibustion device with such a heat transfer metal plate, the above-mentioned action of far-infrared rays, the above-mentioned action of terahertz waves and the above-mentioned action of negative ion are obtained, and further as the penetrated rays of terahertz waves evaporates the loquat-leaf extract to permeate it into the skin, more favorable effects of moxibustion treatment is expected.

The electric moxibustion device of the invention is characterized in that the cap is made of heatproof rubber into which ceramic powder having a record of specific vibration-information is mixed.

From old times, there is an idea that only the 'information' presenting the 'property' of a substance is recorded on water to use the 'information' for treatment. According to the basic idea of a representative example, Homeopathy, when a medical herb extract is repeatedly diluted with water, finally, statistically nothing of molecules of the medical herb but only the 'information' which presents the property of the medical herb remains in the water, and the water, when given to a patient, brings the same effect on the patient as the medical herb does. The 'information' is grasped as 'electron-level vibration' existing in a substance or a living body. The specific vibration-information here means 'vibration-information emitted from a living body only in the condition of continuing living activity' among such 'information'. It is considered that a substance having such a specific vibration-information record has a special revival wavelength and consequently has functions to eliminate harmful matters, mask or eliminate electromagnetic waves and enhance 'life force' which a living body naturally has.

It is known that the substance having a function of transmission of the vibration-information includes water, ore, salt, etc. A method of recording vibration-information on water (refined water) to produce vibration-information recorded water is preciously described in the gazettes PCT/JP2003/010122 and PCT/JP2003/010123. The test, in which 58 subjects drink the vibration-information recorded water for measurement of the stress value before and after drinking, was conducted by using a NIPRO CORPORATION-made enzyme analyzer 'Salivary Amylase Monitor' and the result was published (Table 1).

TABLE 1

| No. | Before Drinking | After Drinking | Difference |
|---|---|---|---|
| 1 | 190 | 23 | 167 |
| 2 | 92 | 19 | 73 |
| 3 | 31 | 19 | 12 |
| 4 | 34 | 19 | 15 |
| 5 | 162 | 48 | 114 |
| 6 | 63 | 16 | 47 |
| 7 | 98 | 22 | 76 |
| 8 | 46 | 20 | 26 |

TABLE 1-continued

| No. | Before Drinking | After Drinking | Difference |
|---|---|---|---|
| 9 | 43 | 33 | 10 |
| 10 | 38 | 35 | 3 |
| 11 | 38 | 19 | 19 |
| 12 | 18 | 18 | 0 |
| 13 | 32 | 20 | 12 |
| 14 | 35 | 17 | 18 |
| 15 | 73 | 22 | 51 |
| 16 | 69 | 15 | 54 |
| 17 | 82 | 21 | 61 |
| 18 | 37 | 22 | 15 |
| 19 | 83 | 17 | 66 |
| 20 | 79 | 4 | 75 |
| 21 | 66 | 23 | 43 |
| 22 | 15 | 13 | 2 |
| 23 | 27 | 14 | 13 |
| 24 | 36 | 14 | 22 |
| 25 | 37 | 25 | 12 |
| 26 | 63 | 8 | 55 |
| 27 | 42 | 27 | 15 |
| 28 | 190 | 34 | 156 |
| 29 | 32 | 27 | 5 |
| 30 | 223 | 42 | 181 |
| 31 | 132 | 40 | 92 |
| 32 | 132 | 35 | 97 |
| 33 | 68 | 29 | 39 |
| 34 | 47 | 14 | 33 |
| 35 | 35 | 7 | 28 |
| 36 | 13 | 9 | 4 |
| 37 | 73 | 32 | 41 |
| 38 | 58 | 22 | 36 |
| 39 | 213 | 69 | 144 |
| 40 | 14 | 6 | 8 |
| 41 | 41 | 23 | 18 |
| 42 | 57 | 4 | 53 |
| 43 | 19 | 15 | 4 |
| 44 | 67 | 29 | 38 |
| 45 | 73 | 66 | 7 |
| 46 | 98 | 38 | 60 |
| 47 | 42 | 20 | 22 |
| 48 | 181 | 81 | 100 |
| 49 | 68 | 40 | 28 |
| 50 | 116 | 19 | 97 |
| 51 | 28 | 19 | 9 |
| 52 | 32 | 20 | 12 |
| 53 | 60 | 14 | 46 |
| 54 | 48 | 10 | 38 |
| 55 | 52 | 6 | 46 |
| 56 | 92 | 37 | 55 |
| 57 | 46 | 40 | 6 |
| 58 | 48 | 27 | 21 |
| Mean Value | 69 | 25 | 45 |

As Table 1 shows, the mean value before drinking of 69 KU/L markedly drops to 25 KU/L after drinking. The most drastically decrease appears in subject No. 30: the stress value of 223 KU/L before drinking the vibration-information recorded water drops to 24 KU/L after drinking. The estimation of the measured value is set as follows:

0-30 KU/L—under no stress;
31-45 KU/L—under a little stress;
46-60 KU/L—under stress; and
61-200 KU/L—under a lot of stress.

Therefore, it can be said that the vibration-information, when taken into a body by drinking the vibration-information recorded water, is effective for reducing stress.

As the electric moxibustion device has the cap made of heatproof rubber into which ceramic powder having a record of such specific vibration-information is mixed, while the cap is applied to the affected part for moxibustion treatment, the vibration-information emitted from the ceramic powder in the cap is taken in the body, thereby masking or eliminating electromagnetic waves causing damage on the human body, restraining stress, and enhancing the life force that the living body naturally has.

The electric moxibustion device is further characterized in that Cymos60-treatment is applied to the ceramic.

The Cymos60-treatment is a treatment to soak an object in the vibration-information recorded water having the above-mentioned vibration-information for about seven days and dry it to record and reserve the same vibration-information on the object. To exemplify that Cymos60-treatment exerts favorable influence to the living body, two kinds of test about Cymos60-treated clothes were carried out. The detail is described below.

First a subject puts on a Cymos60-treated T-shirt and Cymos60-treated socks for measuring the blood flow change of the subject. The measurement was conducted by Technology Research Institute of Osaka Prefecture, Field of Human Body and Sense Measurement. The condition and method of measurement is as follows.

Subject: 5 men
Measuring Instrument: Laser Tissue Blood Flowmeter FLO-C1
Measurement Site: Environmental chamber of 26 degrees C. and 40% humidity
How to Measure:
(1) Enter the environmental chamber wearing ordinary, untreated T-shirt and socks and wait for 15 minutes (in order to adapt to the environment).
(2) Measure the blood flow for 15 minutes (×5 persons).
(3) Change into Cymos60-treated T-shirt and socks.
(4) Carry out the measurement in the order of (1) and (2).

The result of the measurement is shown in Table 2. Each value presents the mean value of 14 times measurement of the blood flow per minute for cells of 100 g.

TABLE 2

| No. | Untreated | Treated |
|---|---|---|
| 1 | 32.26 | 41.05 |
| 2 | 30.53 | 34.77 |
| 3 | 32.57 | 39.65 |
| 4 | 29.60 | 33.52 |
| 5 | 29.87 | 30.07 |

As Table 2 shows, without exception, obviously the subjects have significantly higher blood flow when wearing Cymos60-treated T-shirt and socks. As a result, a hypothesis that Cymos60-treated clothes may contribute to health preservation and promotion can be built up.

In addition to it, with regard to the Cymos60-treated T-shirt, also a test of static electrical propensity (friction-charged electric charge measurement) is conducted by Technology Research Institute of Osaka Prefecture according to a request. The measuring conditions and method is as follows. Table 3 shows the result of the measurement.

Temperature of 20 degrees C.; Humidity of 20% (Condition easy to generate static electricity.)
Testing Method: A testing method in accordance with JIS L 1094.5.3 to make static electricity on a Cymos60-treated T-shirt and an untreated T-shirt (both made of 100% cotton) by rubbing against nylon cloth or acrylic cloth under a load based on JIS (Japanese Industrial Standards), and then calculate the mean value of them (the untreated T-shirt was an ordinary T-shirt on the market).

TABLE 3

|  |  | Treated | Untreated |
|---|---|---|---|
| Nylon friction cloth | lengthwise | 4.7 | 14 |
|  | crosswise | 4.6 | 15 |
| Acrylic friction cloth | lengthwise | 1.3 | 16 |
|  | crosswise | 0.92 | 17 |

Each value above is a mean value. The maximum value regarding the Cymos60-treated T-shirt was 6.5 $\mu C/m^2$ of nylon friction cloth 'crosswise' and the maximum value regarding the untreated T-shirt was 19 $\mu C/m^2$ of acrylic friction cloth 'crosswise'. The value is interpreted as follows.

About 1 $\mu C/m^2$—Electrification amount not enough to feel static electricity
About 5 $\mu C/m^2$—Static electricity generation amount of the degree to gather dusts
Over 10 $\mu C/m^2$—Electrification amount to cause a discomfort static shock As Table 3 shows, it is understood that the amount of static electricity of the Cymos60-treated T-shirt is overwhelmingly smaller than that of the ordinary (untreated) T-shirt. The result proves that Cymos60-treated clothes have a property of generating little static electricity, particularly have a quite high antistatic effect against acrylic cloth.

Consequently, a cap made of rubber into which such Cymos60-treated ceramic powder is mixed emits vibration to activate a living body, so the electric moxibustion device having this cap can exert effects of increasing blood flow and electrostatic prevention as well as a variety of effects mentioned above, thereby being expected to provide a further effective moxibustion treatment.

The absorbent-retentive member can be made of a hygroscopic ring plate with an opening at the center. This is because the opening at the center of the absorbent-retentive member can make the heat from the heat transfer metal plate efficiently radiate to the affected part.

Advantageous Effects of Invention

The electric moxibustion device of the invention is excellent in operability and safety, has an action to thoroughly warm the surface and core of the human body, and can easily permeate effective ingredients of a medical fluid like a loquat-leaf extract under the skin of the affected part, thereby promising a variety of favorable effects on the body such as blood purification, activation of cells, dilation of a capillary, improvement of metabolism, immunity and spontaneous healing power, enhancement of life force, elimination of electromagnetic waves, relief of stress, increase of blood flow, and electrostatic prevention.

DESCRIPTION OF EMBODIMENTS

Figure 1:
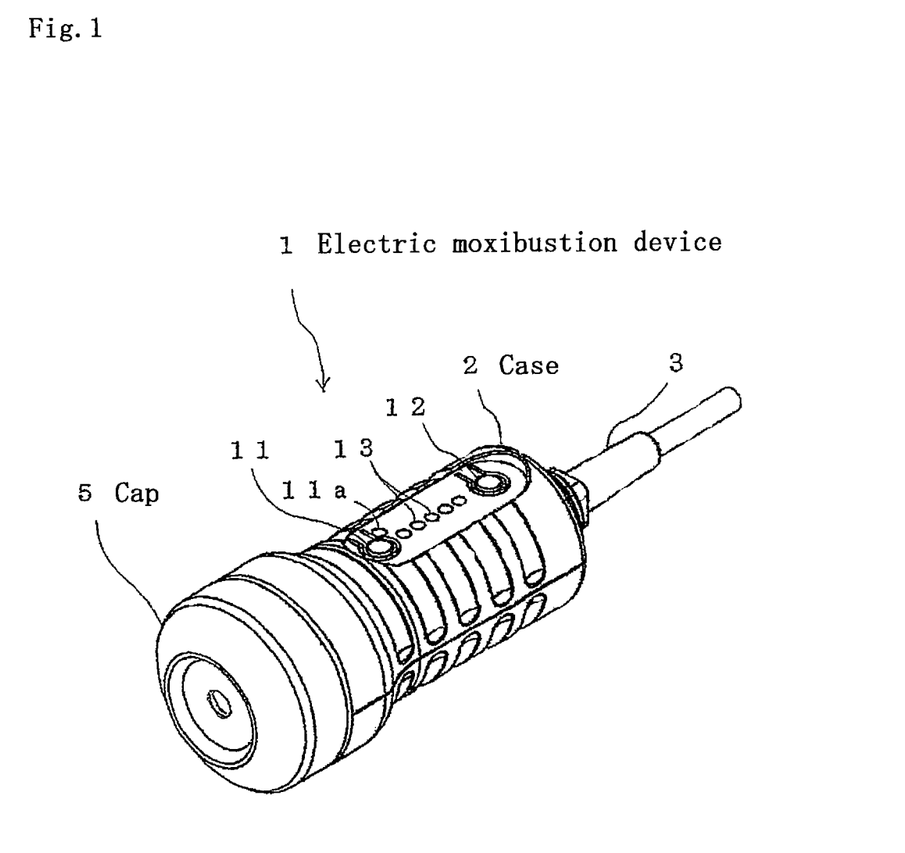
FIG. 1 is a perspective view showing an electric moxibustion device 1 as one embodiment of the present invention.

An electric moxibustion device as one embodiment of the present invention is substantially described below referring to the drawings. FIG. 1 is a perspective view showing the external appearance of the electric moxibustion device 1, FIG. 2 is a cross-sectional view of a heater unit 4 and a cap 5 placed at the front end of the electric moxibustion device 1, and FIG. 3 is an exploded perspective view of the electric moxibustion device 1.

Figure 2:
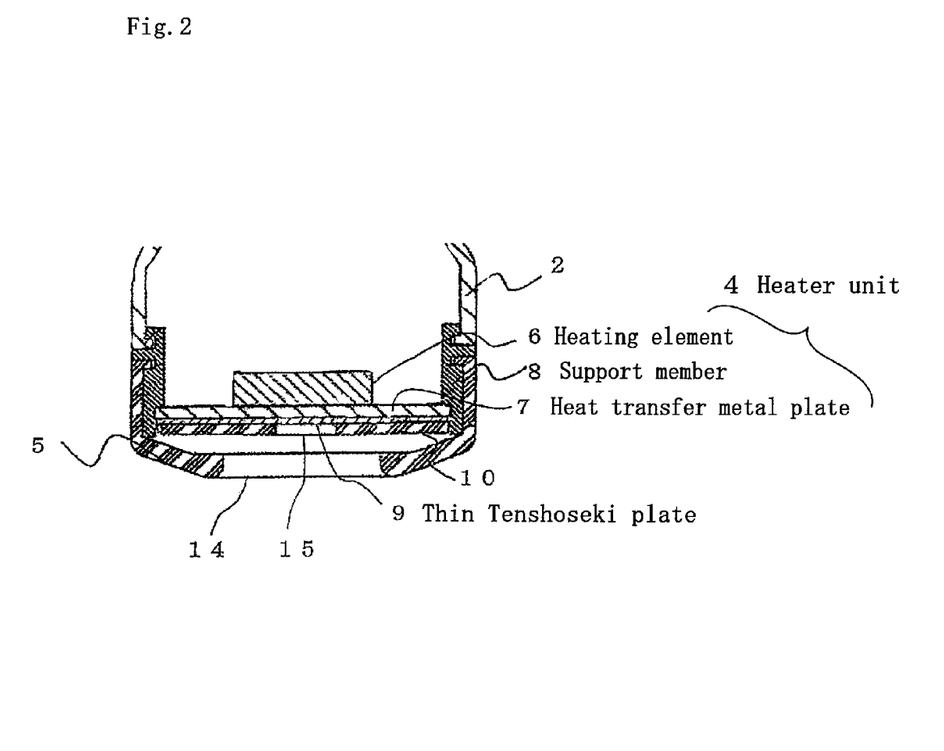
FIG. 2 is a partial expanded cross-sectional view to explain a heater unit 4 and a cap 5 of the electric moxibustion device 1.
Figure 3:
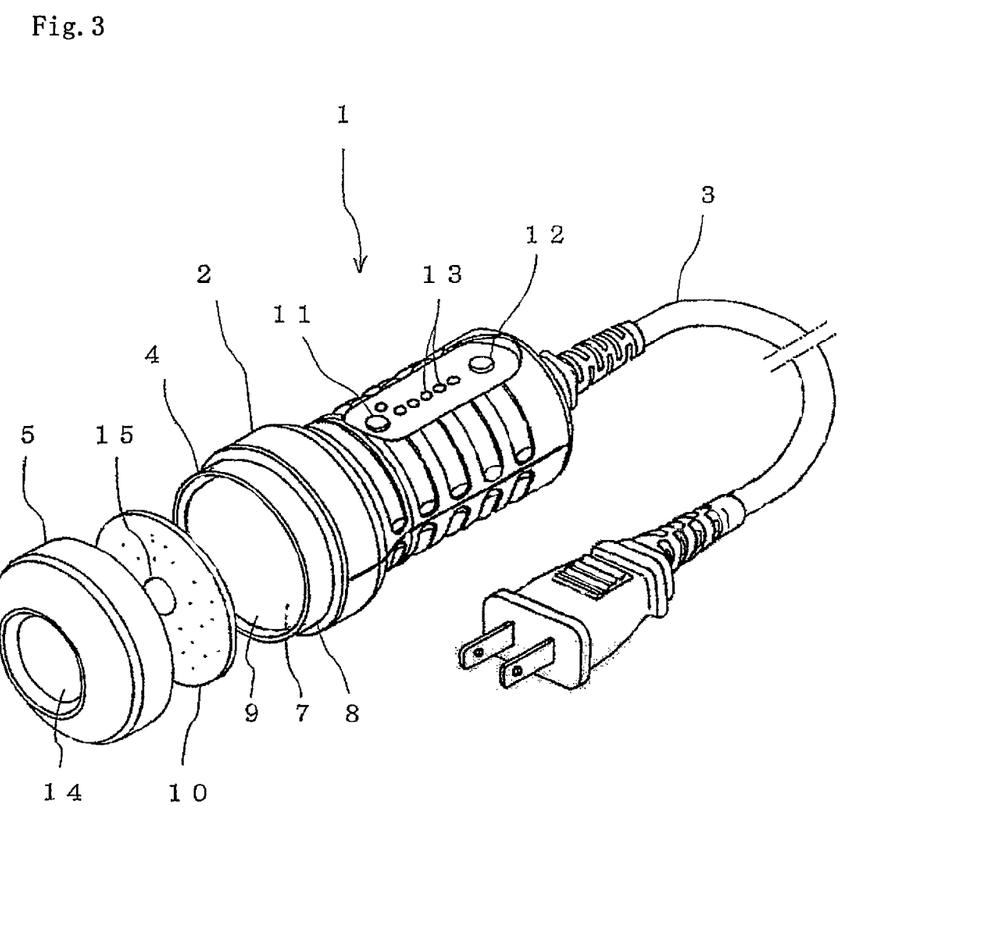
FIG. 3 is an exploded perspective view of the electric moxibustion device 1.

As FIGS. 1-3 show, in the electric moxibustion device 1, a power supply element (a power supply cord) 3 is provided on the rear end of a hollow cylindrical case 2, and a heater unit 4 and a cap 5, which is put against the affected part for heating, are provided on the front end of the case 2. The heater unit 4 has a heating element 6, a heat transfer metal plate 7 and a support member 8. The heating element 6, which is connected to the power supply element 3, is fixed to the back side of the heat transfer metal plate 7. The heat transfer metal plate 7 is integrally formed with the support member 8 and fixed to the case 2 through the support member 8.

The electric moxibustion device 1 has a built-in switching circuit (not illustrated) of power supply and a built-in thermoregulation circuit (not illustrated) for setting the temperature of the heating element 6 in five grades, and is provided with an ON/OFF switching button 11 for power supply, a thermoregulation push button 12, and five temperature indicator lamps 13 on the outer periphery of the case 2. Near the ON/OFF switching button 11, a power supply lamp 11a is installed, which lights when the power supply is ON.

The heat transfer metal plate 7 of the heater unit 4 is made of iron and has a thin Tenshoseki plate 9, which is made in a thin plate-shape, attached to the front surface thereof.

The cap 5 is made of heatproof rubber, into which Cymos60-treated ceramic powder (not illustrated) is mixed. To explain in detail, ceramic powder is soaked in vibration-information recorded water for seven days on which 'a vibration-information emitted from a living body only when continuing living activity', grasped as 'a vibration in the electron level' existing in a substance or a living body, is recorded and preserved in a way described in PCT/JP2003/010123, and dried for recording and preserving the vibration-information (this is Cymos60-treatment), before mixed into the heatproof rubber which forms the cap 5.

A liquid-absorbing cotton ring 10 with an opening 15 in the center, which absorbs and retains a medical fluid such as a loquat-leaf extract, is provided between the heat transfer metal plate 7 and the cap 5.

Additionally a temperature detection circuit and a signal sound output circuit, not illustrated, are installed so as to sound a signal by an electronic buzzer when the temperature of the heating element 6 reaches to the set temperature. Further, a timer circuit, not illustrated, is also installed so as to sound an electronic buzzer 60 minutes after switching on the power supply, turn off the power supply lamp 11a and the temperature indicator lamp 13, and stop automatically.

Followings are the description about how to use the electric moxibustion device 1. Set the liquid-absorbing cotton 10 on the front side of the heat transfer metal plate 7 and fit the cap 5 on the heater unit 4. Infiltrate the liquid-absorbing cotton 10 with a loquat-leaf extract separately prepared. Connect the power supply cord 3 to an electric outlet (not illustrated) and push long the ON/OFF switching button 11 for power supply to switch the power supply on, when the power supply lamp 11a and the middle one among the five temperature indicator lamps 13 are lit. To change the temperature, push long the thermoregulation push button 12 to change the set temperature. Each time pushing long the thermoregulation push button 12, the temperature indicator lamps 13 light one by one to indicate the change of the temperature. When the temperature detection circuit detects the temperature reaching to the set temperature, the signal sound output circuit sounds the electronic buzzer, then push the cap 5 against the affected part to carry out moxibustion treatment.

Besides the above-mentioned embodiment, the electric moxibustion device of the present invention can be carried out as follows.

In the above embodiment, 100V commercial power supply is used for feeding electric power to heat the heating element, but the heating element can be heated also by a direct current fed from a primary or secondary battery which is installed in the case, for example.

The shape of the case is not limited to the cylindrical shape like the above-mentioned embodiment but instead, can be a square tube planed off the corners or a polygonal tube.

| Reference Signs List | |
|---|---|
| 1 | Electric moxibustion device |
| 2 | Case |
| 3 | Power supply cord |
| 4 | Heater unit |
| 5 | Cap |
| 6 | Heating element |
| 7 | Heat transfer metal plate |
| 8 | Support member |
| 9 | Thin Tenshoseki plate |
| 10 | Liquid-absorbing cotton |

What is claimed is:

1. An electric moxibustion device comprising:
a tubular case having a front end opening;
a heater unit placed near the front end opening in the case; and
a heatproof rubber cap removably attached to the front end of said case,
wherein said heater unit comprises a heat transfer metal plate and a heating element which is fixed on the back surface of the heat transfer metal plate and generates heat using power from an external power source or a battery,
wherein said cap has a discharge opening for discharging heat from the heating element, the discharge opening being disposed at the center of the front end of the cap,
wherein said cap and said case are configured for holding an absorbent-retentive member which absorbs and retains a medical fluid between the discharge opening of said cap and said heat transfer metal plate in said case, and
wherein said case has a thermoregulation circuit built-in which can change the temperature of said heating element in a stepwise manner, and push buttons for temperature adjustment are provided on the outer periphery of said case.

2. An electric moxibustion device comprising:
a tubular case having a front end opening;
a heater unit placed near the front end opening in the case; and
a heatproof rubber cap removably attached to the front end of said case,
wherein said heater unit comprises a heat transfer metal plate and a heating element which is fixed on the back surface of the heat transfer metal plate and generates heat using power from an external power source or a battery,
wherein said cap has a discharge opening for discharging heat from the heating element, the discharge opening being disposed at the center of the front end of the cap,
wherein said cap and said case are configured for holding an absorbent-retentive member which absorbs and retains a medical fluid between the discharge opening of said cap and said heat transfer metal plate in said case, and
wherein powdered and granulated ore, which radiate terahertz waves including far-infrared rays when heated, are burned into the surface of said heat transfer metal plate.

3. An electric moxibustion device comprising:
a tubular case having a front end opening;
a heater unit placed near the front end opening in the case; and
a heatproof rubber cap removably attached to the front end of said case,
wherein said heater unit comprises a heat transfer metal plate and a heating element which is fixed on the back surface of the heat transfer metal plate and generates heat using power from an external power source or a battery,
wherein said cap has a discharge opening for discharging heat from the heating element, the discharge opening being disposed at the center of the front end of the cap,
wherein said cap and said case are configured for holding an absorbent-retentive member which absorbs and retains a medical fluid between the discharge opening of said cap and said heat transfer metal plate in said case, and
wherein a thin plate made of ore or powdered and granulated ore, which radiate terahertz waves including far-infrared rays when heated, is glued on the surface of said heat transfer metal plate.

4. The electric moxibustion device of claim 2, wherein said ore is Tenshoseki.

5. The electric moxibustion device of claim 4, wherein negative ion together with terahertz waves including far-infrared rays are radiated from the surface of said heat transfer metal plate.

6. An electric moxibustion device comprising:
a tubular case having a front end opening;
a heater unit placed near the front end opening in the case; and
a heatproof rubber cap removably attached to the front end of said case,
wherein said heater unit comprises a heat transfer metal plate and a heating element which is fixed on the back surface of the heat transfer metal plate and generates heat using power from an external power source or a battery,
wherein said cap has a discharge opening for discharging heat from the heating element, the discharge opening being disposed at the center of the front end of the cap,
wherein said cap and said case are configured for holding an absorbent-retentive member which absorbs and retains a medical fluid between the discharge opening of said cap and said heat transfer metal plate in said case, and
wherein said cap is made of heatproof rubber into which ceramic powder having a record of specific vibration-information is mixed, and Cymos60-treatment is applied to said ceramic.

7. An electric moxibustion device comprising:
a tubular case having a front end opening;
a heater unit placed near the front end opening in the case; and
a heatproof rubber cap removably attached to the front end of said case, wherein said heater unit comprises a heat transfer metal plate and a heating element which is fixed on the back surface of the heat transfer metal plate and generates heat using power from an external power source or a battery, wherein said cap has a discharge opening for discharging heat from the heating element, the discharge opening being disposed at the center of the front end of the cap, wherein said cap and said case are configured for holding an absorbent-retentive member which absorbs and retains a medical fluid between the discharge opening of said cap and said heat transfer metal plate in said case, wherein said case has a thermoregulation circuit built-in which can change the temperature of said heating element in a stepwise manner, and a switch for temperature adjustment and an ON/OFF switch are provided on the outer periphery of said case.

\* \* \* \* \*